(12) United States Patent
Reeder

(10) Patent No.: US 9,182,751 B1
(45) Date of Patent: Nov. 10, 2015

(54) CARBON DIOXIDE MONITORING

(71) Applicant: Alarm.com Incorporated, Vienna, VA (US)

(72) Inventor: Alexander Lawrence Reeder, Arlington, VA (US)

(73) Assignee: Alarm.com Incorporated, Vienna, VA (US)

( * ) Notice: Subject to any disclaimer, the term of this patent is extended or adjusted under 35 U.S.C. 154(b) by 1 day.

(21) Appl. No.: 14/332,682

(22) Filed: Jul. 16, 2014

Related U.S. Application Data

(60) Provisional application No. 61/846,727, filed on Jul. 16, 2013.

(51) Int. Cl.
| | |
|---|---|
| *G08B 17/10* | (2006.01) |
| *G05B 15/02* | (2006.01) |
| *G01N 33/00* | (2006.01) |
| *G08B 21/18* | (2006.01) |

(52) U.S. Cl.
CPC .............. *G05B 15/02* (2013.01); *G01N 33/004* (2013.01); *G01N 33/0063* (2013.01); *G08B 21/182* (2013.01)

(58) Field of Classification Search
CPC .............. H04L 12/2803; G08B 13/194; G08B 21/182; G08C 17/02
USPC ................. 340/632, 628, 506, 514, 541, 523, 340/12.53, 539.13, 539.17
See application file for complete search history.

(56) References Cited

U.S. PATENT DOCUMENTS

| | | | | |
|---|---|---|---|---|
| 6,658,091 | B1 * | 12/2003 | Naidoo ............ | G08B 13/19669 379/37 |
| 7,113,090 | B1 * | 9/2006 | Saylor .............. | G08B 13/19682 340/5.33 |
| 8,630,741 | B1 * | 1/2014 | Matsuoka ........... | H04L 12/2829 700/12 |
| 2010/0277300 | A1 * | 11/2010 | Cohn .................... | G08B 25/001 340/506 |

* cited by examiner

*Primary Examiner* — Tai T Nguyen
(74) *Attorney, Agent, or Firm* — Fish & Richardson P.C.

(57) ABSTRACT

Carbon dioxide monitoring, in which carbon dioxide sensor data is processed in combination with additional sensor and automation control data. A system includes a monitoring system that monitors a fixed property and includes a carbon dioxide sensor, one or more additional sensors that are installed at the fixed property and that sense attributes of the fixed property, and one or more automation control components that control one or more appliances located at the fixed property. The system also includes a monitoring application server that receives data communications based on carbon dioxide sensor data, additional sensor data, and automation control data. The monitoring application server integrates the carbon dioxide sensor data with the additional sensor data and the automation control data, analyzes the integrated carbon dioxide sensor data, additional sensor data, and automation control data, and performs an operation related to the fixed property based on the analysis.

20 Claims, 3 Drawing Sheets

CARBON DIOXIDE MONITORING

CROSS REFERENCE TO RELATED APPLICATIONS

The present application claims the benefit of U.S. Provisional Application No. 61/846,727, filed Jul. 16, 2013, which is incorporated herein by reference in its entirety for all purposes.

TECHNICAL FIELD

This disclosure relates to carbon dioxide monitoring.

BACKGROUND

Many people equip homes and businesses with alarm systems to provide increased security for their homes and businesses. Alarm systems may include control panels that a person may use to control operation of the alarm system and sensors that monitor for security breaches. In response to an alarm system detecting a security breach, the alarm system may generate an audible alert and, if the alarm system is monitored by a monitoring service, the alarm system may send electronic data to the monitoring service to alert the monitoring service of the security breach. In addition, carbon dioxide sensors may be used to sense carbon dioxide levels in an enclosed space.

SUMMARY

Techniques are described for carbon dioxide monitoring. In some examples, carbon dioxide meters may be enabled with wireless communication to identify the use of gas appliances in the home and monitor environmental (e.g., air) quality. In these examples, the carbon dioxide measurement data may be integrated with alarm system data to improve property monitoring and automation technology.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Figure 1:
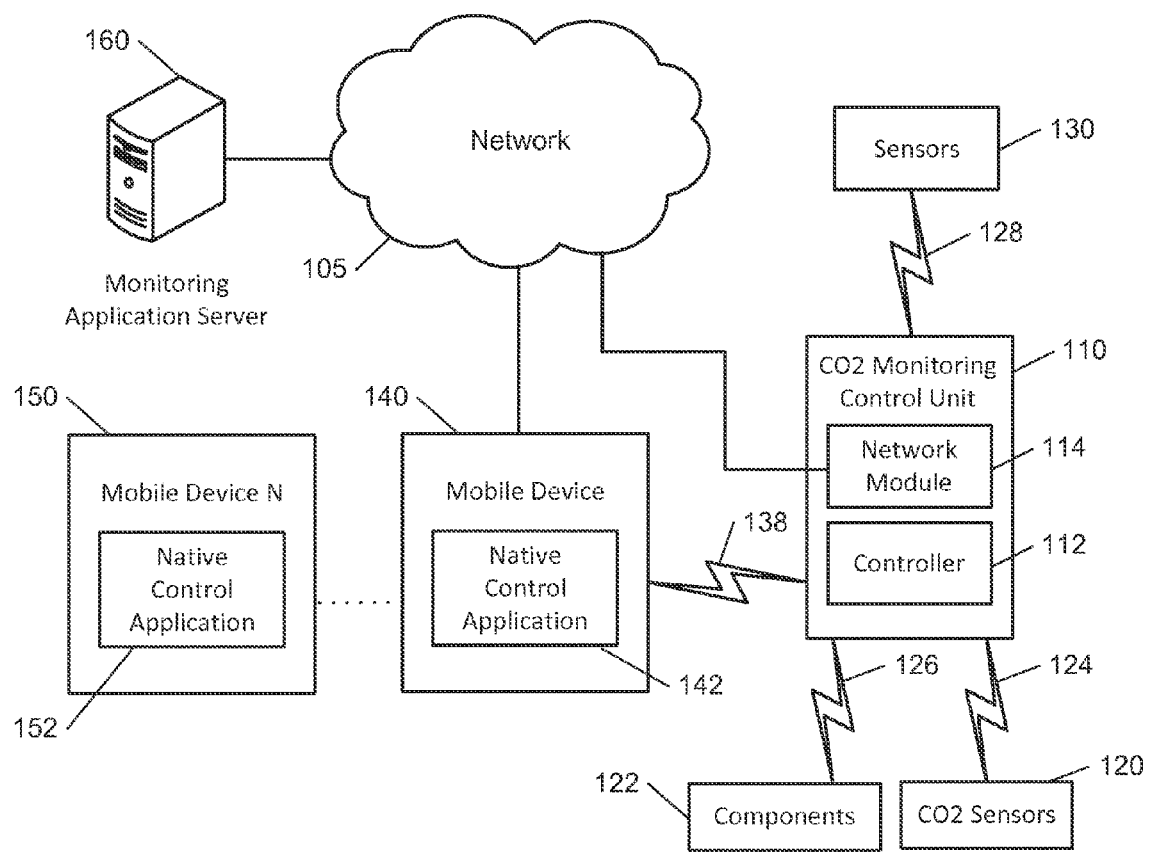
FIG. 1 illustrates an example system.

Techniques are described for providing indoor carbon dioxide ($CO_2$) monitoring and control. In some implementations, a monitoring system that includes a $CO_2$ monitor is able to detect the concentration of $CO_2$ in air within a home, business, vacation, or other property based on data received from sensors within the property. The $CO_2$ concentration is affected by the use of appliances and heating, ventilation, and air conditioning (HVAC) system components that utilize combustion in their operation, such as stoves, ranges, furnaces, generators, etc. The monitoring system analyzes $CO_2$ concentration data and, in some instances, controls appliances or HVAC system components associated with the property to achieve a target $CO_2$ concentration within the property for purposes of air quality control and/or safety control. Furthermore, the monitoring system can use $CO_2$ concentration data to determine the locations and/or physical activity levels of users within the property, based on human users emitting $CO_2$ and emitting increased levels of $CO_2$ when more active. The $CO_2$ concentration data in these instances can be used to generate schedules indicating use of the property and/or resident profiles for the property. Performing analysis of $CO_2$ concentration data can enable an air flow model of the property to be developed that allows users to determine ventilation or insulation faults of the property.

In some implementations, the monitoring system may operate a single $CO_2$ monitoring unit as a disaggregated $CO_2$ sensor that detects $CO_2$ concentrations within different zones of a property. In these implementations, sensors throughout different zones of the property can detect information relating to the concentration of $CO_2$ in the air within each of the zones. Based on determining that a particular zone has experienced a significant change in $CO_2$ concentration, actions can be performed to notify users of the change in $CO_2$ concentration that may be indicative of an event. For example, appliances and/or HVAC system components that utilize combustion, e.g., a stove, range, furnace, generator, etc., can be identified as active based on detecting an increase in $CO_2$ concentration as a result of the appliances and/or HVAC system components performing combustion events, such as the combustion of natural gas that results, for example, from a range that has been turned on. In some instances, appliances or components of an HVAC system can be controlled based on detecting a significant change in $CO_2$ concentration. For example, based on detecting that there has been a decrease in $CO_2$ concentration over a short period of time while the control mechanism for a furnace of a property is set such that the furnace is turned on, the monitoring system can turn off the furnace and notify the resident that the decrease in $CO_2$ may be due to a pilot light of the furnace going out. In practice, other operations can be performed based on detected $CO_2$ levels and/or user inputs, such as user input schedules that indicate target $CO_2$ levels within a property at different times of day.

FIG. 1 illustrates an example of a monitoring system 100 configured to provide dynamic $CO_2$ monitoring and control within a property. The monitoring system 100 includes a network 105, a $CO_2$ monitoring control unit 110, one or more mobile devices 140, 150, and a monitoring application server 160. The network 105 enables communications between the $CO_2$ monitoring control unit 110, the one or more mobile devices 140, 150, and the monitoring application server 160.

The network 105 is configured to enable electronic communications between devices connected to the network 105. For example, the network 105 can be configured to enable the exchange of electronic communications between the $CO_2$ monitoring control unit 110, the one or more mobile devices 140, 150, and the monitoring application server 160.

The network 105 can include, for example, one or more of the Internet, Wide Area Networks (WANs), Local Area Networks (LANs), e.g., Wi-Fi, analog or digital wired and wireless telephone networks, e.g., a public switched telephone network (PSTN), Integrated Services Digital Network (ISDN), a cellular network, and Digital Subscriber Line (DSL), Ethernet, Internet Protocol (IP) over broadband, radio, television, cable, satellite, or any other delivery or tunneling mechanism for carrying data. Network 105 can include multiple networks or subnetworks, each of which can include, for example, a wired or wireless data pathway. The network 105 can include a circuit-switched network, a packet-switched data network, or any other network able to carry electronic communications (e.g., data or voice communications). For example, the network 105 can include networks based on the Internet protocol (IP), asynchronous transfer mode (ATM), the PSTN, packet-switched networks based on IP, X.25, or Frame Relay, or other comparable technologies and can support voice using, for example, VoIP, or other comparable protocols used for voice communications. The network 105 can include one or more networks that include wireless data channels and wireless voice channels. The network 105 can be a wireless network, a broadband network, or a combination of networks including a wireless network and a broadband network.

The $CO_2$ monitoring control unit 110 includes a controller 112 and a network module 114. The controller 112 is configured to control a system, e.g., an HVAC system associated with a property or appliances associated with a property, that includes the $CO_2$ monitoring control unit 110. In some examples, the controller 112 can include a processor or other control circuitry configured to execute instructions of a program that controls operation of appliances or an HVAC system. In these examples, the controller 112 can be configured to receive input from $CO_2$ sensors associated with the monitoring system and control operation of appliances, e.g., a stove, range, furnace, etc., components of an HVAC system, e.g., a furnace, air conditioner, fan, etc., or other devices associated with the property, e.g., windows, ceiling fans, skylights, etc. For example, the controller 112 can be configured to control operation of the network module 114 included in the $CO_2$ monitoring control unit 110.

The network module 114 is a communication device configured to exchange communications over the network 105. The network module 114 can be a wireless communication module configured to exchange wireless communications over the network 105. For example, the network module 114 can be a wireless communication device configured to exchange communications over a wireless data channel. In this example, the network module 114 can transmit $CO_2$ concentration data, user location data within or external to the property, user activity level data within or external to the property, environmental data from the property, e.g., indoors or outdoors at the property, or other data over a wireless data channel. The wireless communication device can include one or more GSM modules, a radio modem, a cellular transmission module, or any type of module configured to exchange communications in one of the following formats: GSM or GPRS, CDMA, EDGE or EGPRS, EV-DO or EVDO, UMTS, or IP.

The network module 114 can also be a wired communication module configured to exchange communications over the network 105 using a wired connection. For instance, the network module 114 can be a modem, a network interface card, or another type of network interface device. The network module 114 can be an Ethernet network card configured to enable the $CO_2$ monitoring control unit 110 to communicate over a local area network and/or the Internet. The network module 114 can also be a voiceband modem configured to enable the $CO_2$ monitoring control unit 110 to communicate over the telephone lines of Plain Old Telephone Systems (POTS). In some implementations, the $CO_2$ monitoring control unit 110 can be a broadband or cellular gateway where the network module 114 can enable the $CO_2$ monitoring control unit 110 to communicate over the network 105.

The monitoring system that includes the $CO_2$ monitoring control unit 110 communicates with the modules 120, 122, and 130 to perform dynamic $CO_2$ concentration monitoring and control at the property. The module 120 is connected to one or more $CO_2$ sensors, e.g., K-30 10,000 PPM 1% $CO_2$ meters from CO2sensor.com, and is configured to monitor $CO_2$ concentrations at the property. The module 120 can communicate $CO_2$ concentration information to or from the $CO_2$ monitoring control unit 110 and can control the $CO_2$ sensors based on commands received from the $CO_2$ monitoring control unit 110.

In some implementations, the module 120 associated with the one or more $CO_2$ sensors can be integrated with the $CO_2$ monitoring control unit 110. For example, the $CO_2$ sensors can include the $CO_2$ monitoring control unit 110, e.g., as an internal component to the $CO_2$ sensors. In some examples, the $CO_2$ monitoring control unit 110 can be a gateway device that communicates with the module 120 associated with the $CO_2$ sensors.

The module 122 is connected to one or more appliances of a property and/or one or more components of an HVAC system associated with a property, and is configured to control operation of the one or more appliances and/or components of the HVAC system. The module 122 can communicate information identifying the status of the appliances and/or HVAC system components to the $CO_2$ monitoring control unit 110 and can control the one or more appliances and/or HVAC system components based on commands received from the $CO_2$ monitoring control unit 110. Although illustrated as a single module 120 and a single module 122, the system 100 may include multiple modules for multiple $CO_2$ monitors and multiple modules for controlling the various components in the system 100.

The module 130 is connected to one or more sensors configured to monitor environmental conditions and/or activity at zones within the property, e.g., at various indoor locations of the property. For example, the sensors connected to the module 130 can include environmental sensors, such as temperature sensors, humidity sensors, noise sensors, light sensors, air quality sensors, smoke detectors, carbon monoxide detectors, water sensors, rain sensors, wind sensors, etc. The sensors can further include sensors for monitoring activity at the property, such as one or more motion sensors, contact sensors, etc. The module 130 connected to the one or more sensors can communicate data obtained by the sensors to the $CO_2$ monitoring control unit 110. For example, the module 130 can transmit sensor data indicating the temperature and the motion of users in a particular room of a home to the $CO_2$ monitoring control unit 110.

The modules 120, 122, and 130 can communicate with the controller 112 over communications links 124, 126, and 128. The communication links 124, 126, and 128 can be wired or wireless data pathways configured to transmit signals from the modules 120, 122, and 130 to the controller 112. The modules 120, 122, and 130 can continuously transmit sensed values to the controller 112, can periodically transmit sensed values to the controller 112, or can transmit sensed values to the controller 112 in response to a change in a sensed value.

In some implementations, the module 122 associated with the one or more appliances and/or one or more components of an HVAC system can communicate indirectly with the $CO_2$ monitoring control unit 110. For example, the $CO_2$ monitoring control unit 110 can communicate with the module 120 to send and/or receive information related to controlling the appliances or components of the HVAC system components, information identifying the status of the appliances or components, e.g., an on or off state, or other information. In some instances, the module 120 associated with the CO2 sensors can communicate information directly to the module 122 associated with the one or more appliances and/or HVAC system components.

The monitoring application server 160 is an electronic device configured to provide monitoring services by exchanging electronic communications with the CO2 monitoring control unit 110 and the one or more mobile devices 140, 150 over the network 105. For example, the monitoring application server 160 can be configured to monitor data obtained by the CO2 monitoring control unit 110. In this example, the monitoring application server 160 can exchange electronic communications with the network module 114 included in the CO2 monitoring control unit 110 to send and/or receive information regarding CO2 concentrations at the property and/or other activity at the property, e.g., activity relating to users of the property and/or use of appliances or HVAC system components associated with the property. The monitoring application server 160 also can receive information regarding CO2 concentrations and/or activity at the property from the one or more mobile devices 140, 150. For example, the monitoring application server 160 can receive information from the one or more mobile devices 140, 150 that indicates the locations of the one or more mobile devices 140, 150.

In some implementations, the monitoring application server 160 can be connected to the Internet over the network 105 and can access information at a website or database that is accessible on the Internet. For example, users associated with a property can specify schedules or preferences relating to CO2 concentration levels within the property at a website or application such that the schedules or preferences are accessible over the network 105. Based on the accessed information, the monitoring application server 150 can communicate with the CO2 monitoring control unit 110 to control CO2 concentrations at the property.

The monitoring application server 160 can store data, e.g., CO2 concentration data, activity data from the property, data associated with user schedules, or data associated with user preferences, and can perform analysis of the stored data. Based on the analysis, the monitoring application server 160 can communicate with and control aspects of the CO2 monitoring control unit 110.

The one or more mobile devices 140, 150 are devices that host one or more native applications, e.g., the native control applications 142, 152. The one or more mobile devices 140, 150 can be cellular phones or non-cellular locally networked devices. The one or more mobile devices 140, 150 can include a cell phone, a smart phone, a tablet PC, a personal digital assistant ("PDA"), or any other stationary or portable device configured to communicate over a network. For example, implementations can also include Blackberry-type devices, e.g., as provided by Research in Motion, electronic organizers, iPhone-type devices, e.g., as provided by Apple, iPod devices, e.g., as provided by Apple, or other portable music players, other communication devices, and handheld or portable electronic devices for gaming, communications, and/or data organization. The one or more mobile devices 140, 150 can be the same or can include mobile devices of different types. The one or more mobile devices 140, 150 can perform functions unrelated to the control system, such as placing personal telephone calls, playing music, playing video, displaying pictures, browsing the Internet, maintaining an electronic calendar, etc.

In some implementations, the one or more mobile devices 140, 150 communicate with and receive control system data from the CO2 monitoring control unit 110 using the communication link 138. For instance, the one or more mobile devices 140, 150 can communicate with the CO2 monitoring control unit 110 using various local wireless protocols, such as Wi-Fi, Bluetooth, Z-Wave, ZigBee, HomePlug (Ethernet over powerline), or wired protocols such as Ethernet, USB, and other wired protocols based on the RS232, RS485, and/or RS422 standards. The one or more mobile devices 140, 150 can connect locally to the control system and its sensors and other devices. The local connection can improve the speed of communications because communicating through the network 105 with a remote server, e.g., the monitoring application server 160, can be slower.

Although the one or more mobile devices 140, 150 are shown communicating with the CO2 monitoring control unit 110, the one or more mobile devices 140, 150 can communicate directly with the sensors and other devices controlled by the CO2 monitoring control unit 110. In some implementations, the one or more mobile devices 140, 150 replace the CO2 monitoring control unit 110 and perform the functions of the CO2 monitoring control unit 110 for local control and long range or offsite communication.

In other implementations, the one or more mobile devices 140, 150 receive control system data captured by the CO2 monitoring control unit 110 through the network 105. The one or more mobile devices 140, 150 can receive the data from the CO2 monitoring control unit 110 through the network 105 or the monitoring application server 160 and can transmit or relay data to the CO2 monitoring control unit 110 or the monitoring application server 160 through the network 105. In this regard, the monitoring application server 160 can facilitate communications between the one or more mobile devices 140, 150 and the CO2 monitoring control unit 110.

Although the one or more mobile devices 140, 150 are shown in FIG. 1 as being connected to the network 105, in some implementations, the one or more mobile devices 140, 150 are not connected to the network 105. In these implementations, the one or more mobile devices 140, 150 communicate directly with one or more of the monitoring system components and no network connection, e.g., connection to the Internet, or reliance on remote servers is needed.

In some implementations, the one or more mobile devices 140, 150 are used in conjunction with only local sensors and/or local devices at a property. In these implementations, the control system 100 only includes the one or more mobile devices 140, 150 and the modules 120, 122, and 130. The one or more mobile devices 140, 150 can receive data directly from the modules 120, 122, and 130 and send data directly to the modules 120, 122, and 130. The one or more mobile devices 140, 150 provide the appropriate interfaces and/or processing to provide for control of the monitoring system, modify monitoring system settings, control the CO2 sensors, control appliances and/or HVAC system components, etc. In some implementations, the one or more mobile devices 140, 150 communicate directly with only the module 120 associated with the CO2 sensors, the module 122 associated with the appliances and/or HVAC system components, and the module 130 associated with the environmental and/or activity sensors to control operation of the appliances and/or system associated with the property.

The one or more mobile devices 140, 150 can each include a native control application 142, 152, respectively. The native control application 142, 152 refers to a software/firmware program running on the corresponding mobile devices that enables the described features. The one or more mobile devices 140, 150 can load or install the native control application 142, 152 based on data received over a network or data received from local media. The native monitoring application 142, 152 can run on mobile devices' platforms, such as Apple iOS, iPhone, iPod touch, Blackberry, Google Android, Windows Mobile, etc.

The described monitoring system enables $CO_2$ concentration levels and trends to be monitored in real time and for appropriate actions to be taken based on reported $CO_2$ concentration levels. Real time monitoring offers an important aspect of property monitoring, as it allows a remote user or system to identify patterns and anomalies in $CO_2$ levels and for appropriate action to be taken if a safety hazard exists or if significant changes in the behavioral patterns of users are detected.

Figure 2:
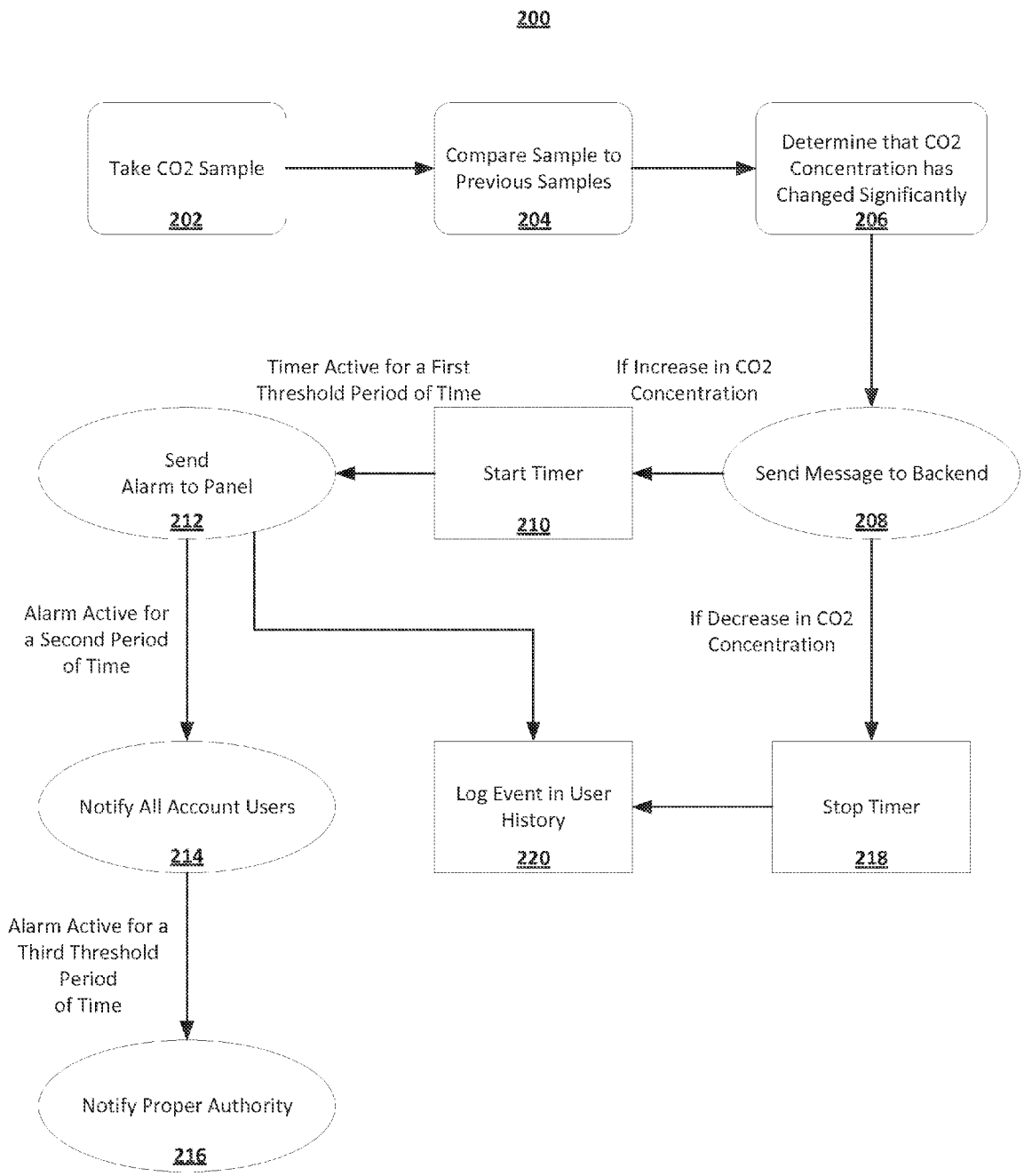
FIG. 2 illustrates an example process performed by a monitoring system based on data received from one or more carbon dioxide sensors associated with the monitoring system.

FIG. 2 illustrates an example process 200 performed by the monitoring system based on data received from one or more $CO_2$ sensors associated with the monitoring system. For example, the steps in the process 200 can be performed in response to receiving $CO_2$ concentration data from sensors of the module 120.

$CO_2$ concentration samples are taken by sensors of the monitoring system (202). For example, $CO_2$ sensors associated with the monitoring system can sample $CO_2$ concentration levels in different zones of a property at regular time intervals such as every minute and can transmit the data identifying the $CO_2$ concentrations to the $CO_2$ monitoring control unit 110. In some implementations, zones can be defined by rooms of a property, or can be defined otherwise based on the number of $CO_2$ sensors that are available.

Based on taking a $CO_2$ concentration sample, a particular sensor can, in some implementations, determine whether to transmit the sample data. For example, to reduce energy used by the sensor in transmitting the sample data, the sensor can determine to send the data only if it indicates a $CO_2$ concentration above a certain threshold, if the change in $CO_2$ concentration from a sample compared to a previous sample is above a certain amount, or based on other criteria.

$CO_2$ concentration samples are compared to previous $CO_2$ concentration samples obtained from $CO_2$ sensors at the property (204). For example, a received set of $CO_2$ concentration data can be compared against the prior $CO_2$ concentration data, to two or more prior sets of $CO_2$ concentration data, or can be compared against $CO_2$ concentration data from a recent time span, e.g., the last 5 minutes or the last one hour. In some implementations, $CO_2$ concentration data can be compared against profiles of $CO_2$ concentration data that indicate historical $CO_2$ concentrations at various zones of a property at various times of day. For example, received $CO_2$ concentration data indicating the concentration of $CO_2$ in the kitchen of a home at 6:00 PM can be compared against historical data indicating $CO_2$ concentrations within the kitchen of the home at 6:00 PM of any given day. In some implementations, comparing a $CO_2$ concentration sample to previous $CO_2$ concentration samples can be performed at the $CO_2$ monitoring control unit 110, or at another component of the monitoring system.

Based on comparing the received $CO_2$ concentration data samples to previous samples, a determination is made whether the $CO_2$ concentration has significantly changed (206). For example, a graph of $CO_2$ concentrations can be maintained, and the received $CO_2$ concentration data and previously received $CO_2$ concentration data can be used to determine a slope of the $CO_2$ concentration graph. Based on the slope of the graph being above a certain magnitude, e.g., based on the concentration of $CO_2$ increasing or decreasing faster than a certain rate, a determination can be made that the $CO_2$ concentration has changed significantly. In some implementations, such a determination can be made for each zone of a property, e.g., for each room of a home, or can be determined for the property as a whole. In some implementations, determining that a $CO_2$ concentration has changed significantly can be performed by the $CO_2$ monitoring control unit 110 of the monitoring system, or at another component of the monitoring system.

Determining that a $CO_2$ concentration has changed significantly can involve determining that a maximum or minimum has occurred in the graph of $CO_2$ concentration for the property. For example, based on two previous $CO_2$ concentration samples indicating that a $CO_2$ concentration is decreasing, and a third $CO_2$ concentration sample that has just been received indicating that the $CO_2$ concentration is now increasing, a minimum point can be identified that corresponds to an event at the property. For example, a maximum or minimum point can be interpreted to correspond to an event in which a user has turned on or turned off a stove in the kitchen of the property, or that a furnace of the property has been turned on or off. Maxima and minima in the $CO_2$ concentration graph for the property correspond to points in the graph of the $CO_2$ concentration in which the slope of the $CO_2$ concentration plot is zero, or in which the slope of the $CO_2$ concentration plot has changed from a positive slope to a negative slope, or from a negative slope to a positive slope.

In some implementations, determining that a $CO_2$ concentration has changed significantly can involve determining that an inflection point has occurred in the graph of $CO_2$ concentration for the property. For example, based on three previous $CO_2$ concentration samples indicating that a $CO_2$ concentration is increasing at a decreasing rate, e.g., leveling off, a fourth $CO_2$ concentration sample that has just been received indicating that the $CO_2$ concentration is now increasing at an increasing rate, an inflection point can be identified that corresponds to an event at the property. For example, an inflection point can indicate that a user has turned on or turned off a stove in the kitchen of the property, or that a furnace of the property has been turned on or off. Inflection points correspond to the zeroes of the second derivative of the graph of $CO_2$ concentration at the property. Such inflection points are easily determined through basic processing of $CO_2$ concentration data. Combustion-related events will almost always correspond with the zeroes of the first and/or second derivatives of the plot of the $CO_2$ concentration data.

In some implementations, determining that a $CO_2$ concentration has changed significantly can involve determining that the $CO_2$ concentration is outside of an acceptable range or is outside of a typical range when compared to historical $CO_2$ concentration data. For example, a threshold $CO_2$ concentration can be 4000 parts per million (PPM), and based on the $CO_2$ concentration sample indicating that the $CO_2$ concentration is above the 4000 PPM threshold, a determination can be made that the $CO_2$ concentration has changed significantly. In another example, historical data may indicate that at 6:00 PM in the kitchen of a home the typical $CO_2$ concentration is 3000 PPM. In this example, based on determining that a $CO_2$ concentration sample indicates that the $CO_2$ concentration is above the typical level by a threshold amount, a determination can be made that the $CO_2$ concentration has changed significantly.

A message is transmitted based on determining that a $CO_2$ concentration has changed significantly (208). For example, based on determining that $CO_2$ concentrations in the kitchen of a home have increased significantly over a period of ten minutes, a message can be transmitted to an application indicating the significant increase in $CO_2$ concentration. In some instances, the message can identify a possible rationale for the significant change in $CO_2$ concentration. For example, a message can indicate that $CO_2$ concentrations in a kitchen of a home have increased significantly and can indicate that a likely reason for the increase is that a user of the kitchen turned on a range. In some implementations, the message can be transmitted by the CO2 monitoring control unit 110 to the monitoring application server 160 over the network 105. Additionally or alternatively, the message can be transmitted to an application operating on a mobile device 140, 150, or to another location, for example, an online monitoring service application accessible over the network 105.

In some implementations, a message is sent only if the condition associated with the significantly changed CO2 concentration persists for a period of time, or based on another condition being satisfied. For example, to conserve energy resources of a CO2 sensor by avoiding transmitting messages over the network 105, the CO2 sensor may only transmit a message if the condition associated with the significantly changed CO2 concentration has persisted for a period of at least five minutes. In another instance, messages may only be sent when users are located away from the property, or only when users are located at the property. By avoiding sending messages unnecessarily, energy used in transmitting the message can be conserved. For example, a battery operated CO2 sensor can conserve the energy required to send a transmission and therefore operate for a longer time span if the CO2 sensor does not transmit messages relating to false CO2 concentration samples or transient CO2 concentration events, e.g., events in which a CO2 concentration is above a threshold for only a very short period of time.

Based on a message indicating that a CO2 concentration has significantly increased, a timer is started (210). For example, based on determining that the CO2 concentration within a kitchen of a home has significantly increased over a period of time, a timer can be started that measures the amount of time since the CO2 concentration was determined to have changed significantly. In some implementations, the timer can be maintained at the CO2 monitoring control unit 110, at the monitoring application server 160, or at another location, such as a mobile device 140, 150 or at a website or server that is accessible over the network 105.

If a timer has remained active for a predetermined period of time in association with the detected significant increase in CO2 concentration, an alarm is provided for display at a panel associated with the CO2 sensor, CO2 monitoring control unit 110, or another component of the monitoring system (212). For example, based on the timer associated with detecting a significant increase in CO2 concentration in a kitchen of a home being active for one hour without being deactivated due to detecting a counteracting significant decrease in CO2 concentration, an alarm can be provided for output at a panel associated with the CO2 sensor or CO2 monitoring control unit 110. Such an alarm can be a visual alarm, e.g., an image or text, an audible alarm, e.g., a siren or spoken voice alarm, or can be any other form of alert provided for output to users of the monitoring system. In some implementations, an alarm can be provided based on the timer being active for a period of minutes, a period of hours, or an extended period of one or more days. In some implementations, a timer can be associated with the CO2 sensor, e.g., the CO2 sensor associated with the module 130, and the alert can be provided for output at a panel of the CO2 sensor based on the timer expiring.

In some implementations, a timer is maintained at a monitoring application server 160, one or more mobile devices 140, 150, or at another location accessible over the network 105, and based on a predetermined period of time passing, a message can be sent that causes the alarm to be output to the panel. For example, if a timer maintained at a monitoring application server 160 is active for longer than a threshold period of time, the monitoring application server 160 can transmit a message to the CO2 monitoring control unit 110 that, in turn, causes an alert to be output at a panel of the CO2 monitoring control unit 110 or of the one or more CO2 sensors. For instance, the transmitted message can be a message that causes the one or more CO2 sensors to provide previously stored alarms for output at one or more panels of the CO2 sensors, or the message can contain data associated with the alarm, e.g., data associated with text that is provided for output at the panels in association with the alarm.

Based on a second threshold period of time being surpassed, users of a property can be notified of the significant change in CO2 concentration (214). For example, based on an additional period of one hour passing since the initial determination of the significant change in CO2, i.e., a total of two hours since the determination that the CO2 concentration has significantly changed, an alarm can be provided for output to users of the property indicating the significant change in CO2 concentration. In some implementations, providing a notification to users of a property can involve providing a notification or alarm for output at a mobile device 140, 150 of each user associated with the property.

For example, based on a monitoring application server 160 determining that the second period of time has been surpassed, the monitoring application server 160 can transmit a message to the mobile devices 140, 150 over the network 105 indicating that a notification should be provided for output at the mobile devices 140, 150. Such a message can cause the mobile devices 140, 150 to output a predetermined or stored notification, or the message can contain data relevant to the output notification. Alternatively or in addition to providing a notification at a mobile device 140, 150 of a user, a notification can be provided to a user using other communication technologies, for example, by sending the user an email, a message in a social network, an automated phone call, a message at an application associated with the monitoring system, or other notifications indicating the significant change in CO2 concentration at the property.

Based on a third threshold period of time being surpassed, the monitoring system can notify proper authorities of the significant increase in CO2 concentration (216). For example, based on an additional one hour passing since the second determination to notify the users of the significant change in CO2 concentration, i.e., a total of three hours since the determination that the CO2 concentration has significantly changed, authorities can be notified regarding the CO2 levels at the property. In some instances, proper authorities may include a property manager or management service, emergency services, such as a fire department, police department, or emergency medical service (EMS), or can be any other authority. In some implementations, the proper authorities can be provided information related to the detected significant change in CO2 concentration, e.g., the current CO2 concentration within the property, the location within the property of the increased CO2 concentration, information identifying users of the property or indicating whether any users are believed to be present at the property, etc. In some instances, the proper authorities are notified through a connection over the network 105, for example, based on the CO2 monitoring control unit 110 or monitoring application server 160 sending a message over the network 105 to a computing system associated with the proper authority.

In some implementations, in response to detecting a significant change in CO2 concentration, different operations can be performed by the monitoring system. For example, a monitoring system that is able to control appliances associated with a property and/or components of an HVAC system associated with a property can detect the significant change in CO2 concentration at the property and can control appliances and/or HVAC system components based on the detection. For instance, based on determining that the CO2 concentration in a kitchen of a home has significantly increased, the monitoring system can turn off a stove and range in the kitchen. The system may turn off the stove and range in the kitchen of the property for the purpose of reducing the energy consumption by the stove and range, or may turn off the stove and range to mitigate the fire hazard posed by the stove and range when they are turned on.

In some examples, the monitoring system can receive information that identifies the status of appliances and/or HVAC system components, and can control the appliances and/or HVAC system components based on their status. For example, based on a stove of a home being on, but a range of a home being off, the monitoring system can determine to only turn off the stove in response to detecting a significant increase in CO2 concentration. In some instances, the monitoring system can determine that a significant change in CO2 concentration has occurred at the property and can correlate the significant change with a status change for an appliance or component of an HVAC system. For example, the monitoring system can detect that a significant change in CO2 concentration has occurred at 6:30 PM and can also determine that a stove was turned on in the property one half hour prior at 6:00 PM. The monitoring system can determine that the stove is a likely cause of the significant change in CO2 concentration at the property, and can turn off the stove in response to the significant change in CO2. The monitoring system can otherwise determine to control appliances and/or HVAC system components based on detecting a significant change in CO2 concentration, for example, by turning off or otherwise controlling all or a subset of the appliances and/or HVAC system components that are turned on at the time of detecting the significant change.

In certain applications of home monitoring, resident behavior is one of the metrics being tracked. For example, the eating habits of an elderly home-care patient are often used as indicators of general well-being. Based on CO2 concentration data indicating when a stove or range is turned on at the property, cooking habits of a resident of the property can be monitored. Monitoring the deviations in cooking habits can indicate whether a patient has forgotten to cook dinner or has lost her appetite, both potential warning signs of illness.

In some cases, the monitoring system can determine an appliance or HVAC system component to control based on the amount of time that the device has been turned on, e.g., based on a likelihood that the appliance or component was accidentally left on by a user. For example, based on detecting a significant change in CO2 and also determining that a stove in the property has been turned on for a period of 3 hours, the monitoring system can determine that it is likely that a user of the property accidentally left the stove turned on and can turn off the stove or notify users of the property that the stove will be turned off unless an action is taken by a user. In this example, a notification can be provided to users indicating that the stove will be turned off, and the users can decline to have the stove turned off if it is still being used.

The monitoring system also may control appliances and/or HVAC system components based on detecting a significant change in CO2 concentration and also determining that an error or fault may exist with a particular appliance or HVAC system component. For example, a significant change in CO2 concentration at a property is detected, and the monitoring system further determines that, despite a furnace of the property being turned on for the past two hours, the temperature in the property has not increased appropriately. Based on determining that the furnace has been operating for two hours without significantly affecting the temperature in the property, the monitoring system can determine that an anomaly may exist within the system or the property. For example, a door or window of the property may have been left open, or there may be a blockage or failure in the duct work. In other implementations, the system may determine errors or faults in another way, and may control the appliances or HVAC system components of a property based on detecting such issues and/or detecting significant changes in CO2 concentration.

In some implementations, the monitoring system may be associated with a rule engine that is used to determine a response to a significant change in CO2 at the property. For example, the rule engine can specify a response that includes providing particular notifications or controlling one or more appliances and/or HVAC system components associated with the property. In some instances, the rule engine can determine the response based on one or more of a trigger event that corresponds to a significant change in CO2 concentration, a timeframe of the significant change in CO2 concentration, and/or a zone of the property associated with the significant change in CO2 concentration. For instance, a rule engine can include a rule specifying that, if a significant change in CO2 concentration is detected on weekdays between 9:00 AM and 5:00 PM at any location of the property, the monitoring system should turn off the furnace of the property. As another example, the rule engine can include a rule specifying that if a significant change in CO2 concentration is detected on any day between 5:00 PM and 11:30 PM at any location of the property, the monitoring system should turn on a vent fan associated with the property and should furthermore provide an alert to all mobile devices associated with users of the property.

Based on the monitoring system detecting a significant decrease in CO2 concentration, any running timer that has been activated as a result of a significant increase in CO2 concentration can be stopped (218). For example, a previously detected significant increase in CO2 concentration at the property may have an associated timer that indicates the amount of time that has passed since the significant increase was detected. Based on detecting a subsequent significant decrease in CO2 concentration, the timer can then be stopped, thereby indicating that the event related to the increased CO2 concentration has passed. In some instances, a significant decrease in CO2 concentration can be detected after the monitoring system has reacted to a significant increase in CO2 concentration at the property. For example, a significant decrease in CO2 concentration can be detected after the monitoring system has detected a significant increase in CO2 concentration and in response turned off a stove and turned on a ventilation fan associated with the property.

After determining that a significant change in CO2 concentration has occurred and a duration of the event associated with the significant change in CO2 concentration, an event can be logged by the monitoring system that is associated with the detected significant change in CO2 concentration (220). For example, based on determining that a significant decrease in CO2 concentration has occurred and that a timer associated with a prior significant increase in CO2 concentration has been stopped, the monitoring system can log information associated with the detected significant changes in CO2 concentration at the property. In another example, a significant increase in CO2 concentration can be detected, and based on a threshold period of time passing and/or an alarm associated with the detected increase in CO2 concentration being broadcast, information relating to the identified increase in CO2 concentration can be logged.

Figure 3:
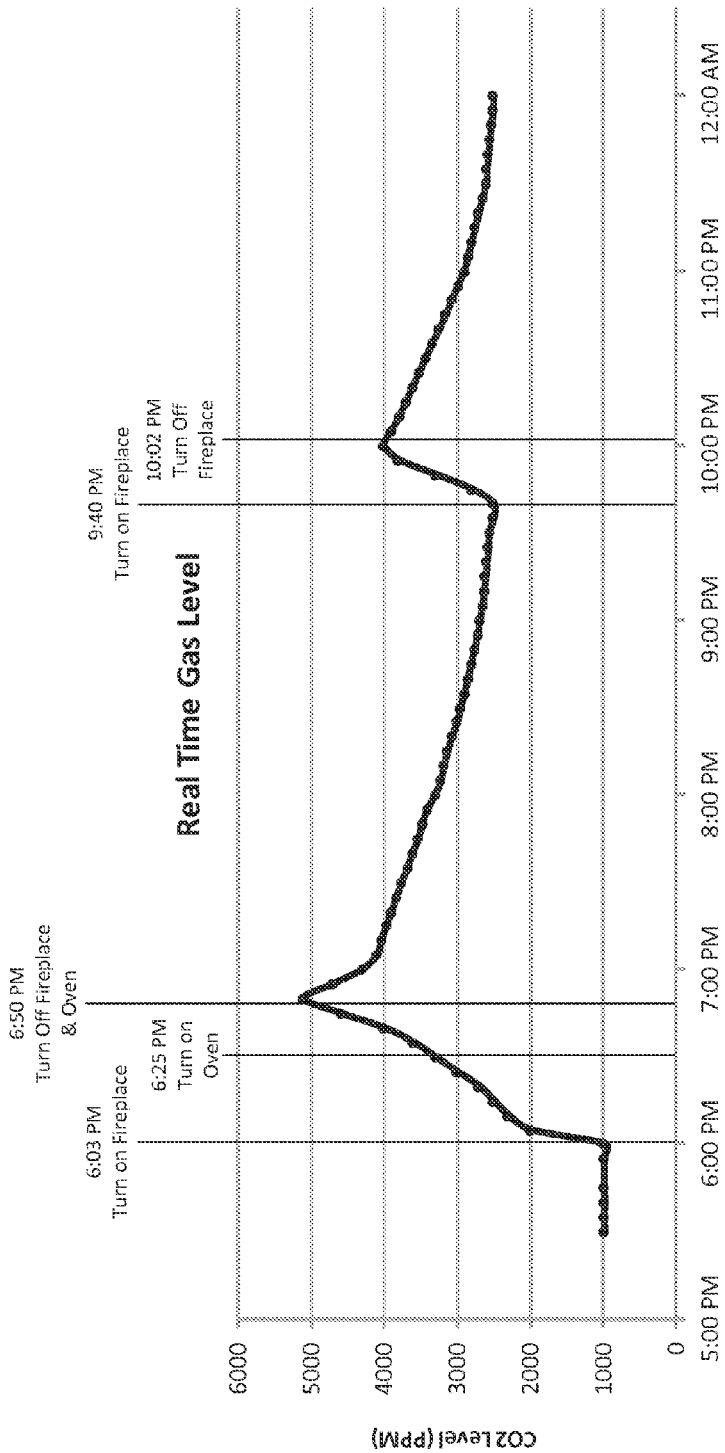
FIG. 3 illustrates an example graph of carbon dioxide concentrations within a property.

FIG. 3 depicts an example graph 300 of CO2 concentrations within a property. For example, the graph 300 can be obtained based on a CO2 sensor associated with the monitoring system obtaining CO2 concentration data at a regular interval, e.g., every five minutes. The CO2 concentration data can be transmitted to and analyzed by the CO2 monitoring control unit 110, the monitoring application server 160, or another component of the monitoring system.

The graph 300 includes CO2 concentration data over a period of 6.5 hours from 5:30 PM to 12:00 AM on a particular day. For example, the CO2 concentration data can show CO2 concentration data obtained by one of the sensors of the monitoring system 100, or can be an average of CO2 concentration data obtained by multiple CO2 sensors in a particular zone of a property or of all of the CO2 sensors within a property. The CO2 PPM concentration is obtained by the one or more CO2 sensors at regular intervals, e.g., every five minutes, and is transmitted for analysis. For example, the monitoring application server 160 can receive the CO2 concentration data from the one or more CO2 sensors and can plot the CO2 concentration data on the graph 300 that depicts CO2 concentration (PPM) versus time for a specific period of time, e.g., 5:30 PM to 12:00 AM. In some implementations, analysis performed on the CO2 concentration data can exclude outliers in the data, e.g., data points that are greater than one standard deviation above or below a previously detected CO2 concentration level can be excluded from the graph. In some implementations, a line of best fit, running average, linear regression, or other analysis can be performed on the CO2 concentration data to obtain additional information about a rate of change of CO2 concentration, e.g., a slope of the curve at some point in time. For example, the analysis can be used to determine maxima and minima in the CO2 concentration data, e.g., points when the slope of the CO2 concentration data is zero, changes from a positive slope to a negative slope, or vice versa, or to determine inflection points in the CO2 concentration data, e.g., points in the CO2 concentration data when the slope of the curve changes from an increasingly positive slope to a decreasingly positive slope or vice versa, or from an increasingly negative slope to a decreasingly negative slope or vice versa, or to determine other characteristics of the CO2 concentration data. In some instances, CO2 concentration data is plotted and analyzed by the monitoring system in real time, e.g., as the CO2 sensors sample the CO2 concentration within the property, or can be performed after the CO2 concentration has been collected, e.g., once per day.

In some implementations, changes in CO2 concentration that are plotted in the graph 300 are associated with events occurring at the property. For example, the monitoring system can determine that certain appliances or HVAC system components are turned on or off at the property, and can correlate changes in CO2 concentration at the property to the turning on and off of the appliances or HVAC system components. As shown in the graph 300, a sudden increase in CO2 concentration at the property beginning at 6:02 PM is correlated with a gas fireplace within the property being turned on. For example, the CO2 monitoring control unit 110 can detect at 6:02 PM that a user of the property has turned on the gas fireplace, and can report this activity to the monitoring application server 160 over the network 105. The monitoring application server 160 can plot received CO2 concentration data and correlate the increase in CO2 concentration that begins to occur at 6:02 PM with the turning on of the gas fireplace. Similarly, a second increase in CO2 concentration that is detected at 6:25 PM can be correlated with a user of a property turning on an oven at the property. For example, the CO2 monitoring control unit 110 can receive information indicating that the oven at the property has been turned on, and can transmit data indicating that the oven has been turned on to the monitoring application server 160. The monitoring application server can then correlate the increase in rate of change of CO2 concentration in the property that begins to occur at 6:25 PM with the turning on of the oven that occurred at the same time.

At 6:50 PM, the graph 300 of the CO2 concentration data shows an inflection point in which the CO2 concentration within the property begins to decrease. Based on data indicating that the gas fireplace and oven were turned off at approximately 6:50 PM, the monitoring system can correlate the change in CO2 concentration and the difference in rate of change in the CO2 concentration, e.g., changing from an increasing slope to a decreasing slope, to the turning off of the gas fireplace and oven. After the gas fireplace and oven are turned off, the CO2 concentration continues to decrease within the property as air turnover takes place. For example, an HVAC system operating at the property, open doors and/or windows, and/or a circulation or ventilation fan operating at the property can cause the CO2 concentration within the property to decrease as new air having lower concentrations of CO2 are mixed with the CO2 laden air within the property. The CO2 concentration can continue to decrease, for example, in a linear or exponential fashion as depicted in the graph 300, or can various other profiles depending upon the property and other factors. In some instances, the rate of decrease of the CO2 concentration within the property can be analyzed to estimate a rate of turnover of air within the property. In some implementations, multiple graphs similar to the graph 300 can be compared or otherwise analyzed to determine an air flow model for a property, or to determine other ventilation characteristics of a property, e.g., leaks in insulation, windows, or doors of the property, areas where insufficient air circulation occurs, etc. Similar to the events detected and described previously, CO2 concentration data obtained at 9:40 PM can indicate that a sudden increase in CO2 concentration has occurred, which can be correlated by the monitoring system to a user of the property turning on a gas fireplace of the property. At 10:02 PM, the rate of change in CO2 concentration can change from an increasing rate to a decreasing rate, which can be correlated to the gas fireplace being turned off once again.

In some implementations, information associated with a detected event can be logged at a profile associated with a particular property or set of users of the property. The information logged in the profile can include dates and times associated with the detected event, the duration of the detected event, CO2 concentration levels in the property at the times of the detected event, a response of the monitoring system to the detected event, locations within the property associated with the detected event, etc.

Information in the profile can then be used to improve CO2 concentration control within the property. For example, the information from the profile can be used to determine patterns of CO2 concentration events for the property, and the monitoring system can adjust control of appliances and/or HVAC system components associated with the property based on the patterns of CO2 concentration. In another example, the monitoring system can monitor the efficacy of specific responses to significant changes in CO2 concentration, e.g., how effective turning on a ventilation fan is in comparison to automatically opening a skylight of a property, and adjustments can be made to how the monitoring system reacts to future significant changes in CO2 concentration based on the efficacy information. In further examples, profile information can indicate typical causes for changes in CO2 concentration associated with different times of day, and the monitoring system can react to changes in CO2 concentration differently depending upon the time of day.

For example, the monitoring system can determine that a significant change in CO2 concentration detected at 6:00 PM is typically due to a stove being turned on and can determine to react to all significant changes in CO2 that occur around 6:00 PM and last for more than a threshold period of time by turning off the stove. Meanwhile, the monitoring system can determine that significant changes in CO2 concentration detected after 10:00 PM are typically due to the operation of a furnace of the property, and thus the monitoring system can react to significant CO2 concentration changes that occur after 10:00 PM and last for more than a threshold period of time by turning off the furnace. In some implementations, additional factors can contribute to determining a reaction to a significant change in CO2 concentration. For example, based on determining that a significant change in CO2 concentration has occurred after 10:00 PM, the monitoring system can access data indicating information, such as an indoor temperature in the property and an outdoor temperature at the property. The indoor and outdoor temperatures can indicate information relevant to determining a response to the significant change in CO2 concentration, e.g., an indoor temperature that is far from a target indoor temperature set at a thermostat can indicate that the furnace is malfunctioning and should be turned off, while a low outdoor temperature can be used to determine that the residents of the property require the furnace to heat the property and thus that the furnace should remain on.

Similarly, profile information may indicate that certain changes in CO2 concentration are typically detected in connection with a particular user or group of users of a property, and the monitoring system can react differently to changes in CO2 concentration depending upon the nature of a detected change in CO2 concentration. For example, profile information can indicate that a particular user is typically home when significant changes in CO2 concentration are detected as a result of a stove being turned on for an extended period of time, indicating that the user may have a habit of leaving the stove turned on after use. Based on the profile data, if a significant change in CO2 concentration is detected in connection with the stove being turned on, the monitoring system may determine to send a notification to a mobile device associated with the particular user before sending a notification to any other user of the property.

In some implementations, the monitoring system can monitor and perform operations based on a combination of CO2 concentration data and other data obtained from a property. For example, the monitoring system can include other sensors, such as temperature, humidity, ambient light, motion, or sound sensors, and can use information provided by those other sensors to determine actions to perform. A monitoring system that includes both CO2 concentration and temperature sensors, for instance, can detect that a significant change in CO2 concentration has occurred while the temperature within the property has deviated further from a target temperature input at a thermostat, e.g., a thermostat is set to 70° F. in the winter and the temperature in the property has changed from 70° F. to 65° F. within a short period of time. Based on determining that the furnace controller indicates that the furnace should be on, and that the CO2 concentration in the furnace room has risen, the monitoring system can notify the resident that there is a door or window open or a blockage in the duct work. If there is no increase in CO2 concentration, the monitoring system can determine that there is likely no combustion in the furnace, and can notify the resident and/or turn off the furnace.

In some implementations, the monitoring system is used to perform air quality monitoring and control at the property in addition to detecting potential safety hazards relating to CO2 concentrations at the property. A monitoring system may recognize a target CO2 concentration for the property that is an ideal CO2 concentration, and the monitoring system can observe CO2 concentrations at the property in reference to the target concentration and/or perform operations to achieve the target concentration at the property. For example, the monitoring system can acknowledge an ideal CO2 concentration of 600 PPM and can monitor CO2 concentrations at the property in reference to the 600 PPM target concentration or can perform operations to direct the CO2 concentration within the property towards the 600 PPM target. For instance, the monitoring system can determine that the CO2 concentration within the property is approximately 800 PPM, and can activate a ventilation fan in the property in an effort to direct the CO2 concentration towards the 600 PPM target.

In some implementations, users associated with a property can establish a schedule indicating target CO2 concentrations within the property. For example, a user can specify that, for any given day, maximum CO2 concentrations within the property are 1500 PPM from 12:00 AM to 7:00 AM, 1000 PPM from 7:00 AM to 1:00 PM, 1500 PPM from 1:00 PM to 7:00 PM, and 2000 PPM from 7:00 PM to 12:00 AM. Depending upon the time of day, the monitoring system can then monitor the CO2 concentration within the property in reference to the current target CO2 concentration or can control appliances and/or HVAC system components associated with the property to achieve the current target CO2 concentration within the property. In some implementations, users can identify target CO2 concentrations and/or schedules relating to target CO2 concentrations by using a panel associated with a CO2 monitor, by using an application accessible at a mobile device 140, 150, or by using another application or interface, where the information related to the target CO2 concentration is available to the monitoring system locally or over the network 105.

The monitoring system can also acknowledge schedules of use for appliances and/or HVAC system components in monitoring and achieving target CO2 concentrations within a property. For example, the monitoring system can acknowledge typical usage schedules for a furnace of a home, a stove, and a range. Based on the schedules, the monitoring system can determine that changes in CO2 concentration within a home are attributable to the use of a particular appliance or HVAC system component. For example, based on a schedule indicating that a range is typically used between the hours of 6:00 PM and 7:00 PM, a detected increase in CO2 concentration at 6:30 PM can be identified as likely corresponding to use of the range in the property.

In some implementations, the monitoring system can control appliances and/or HVAC system components based on a schedule indicating planned usage of certain appliances and/or HVAC system components. For example, if a target CO2 concentration is identified as 1000 PPM and a current CO2 concentration in the home is 950 PPM but a schedule indicates that a range is likely to be used within the near future, the monitoring system can determine to turn on a ventilation fan of the property to reduce the chance that use of the range in the near future will cause the CO2 concentration target to be exceeded.

In addition to acknowledging schedules that indicate likely times of use of appliances and/or HVAC system components, the monitoring system can also acknowledge schedules indicating off-limit times of use and/or time limits associated with the use of appliances and/or HVAC system components. For example, schedules can indicate that a range should not be turned on after 11:00 PM and, based on the monitoring system determining that the range is still turned on after 11:00 PM, the monitoring system can turn off the range. In a similar scenario, a schedule may indicate that the range should never be active for more than three hours at a time, and based on determining that the range has been turned on for longer than three hours, the monitoring system can turn off the range.

In some implementations, the monitoring system may be capable of controlling appliances and/or HVAC system components associated with a property by communicating with the appliances and/or components over established communications channels. For example, the monitoring system may be able to communicate with appliances or HVAC system components that are equipped with wireless or wired communication capabilities, e.g., that can communicate over Wi-Fi, Z-Wave, ZigBee, Bluetooth, HomePlug, Ethernet, USB, or other wired protocols based on the RS232, RS485, and/or RS422 standards. In some instances, the monitoring system may be able to control the appliances and/or HVAC system components indirectly through another component of a home system. For example, the monitoring system may be able to control a furnace of a property by communicating with a thermostat of the property that is responsible for controlling the furnace. In some instances, the monitoring system could control the furnace by using the thermostat to turn on the furnace, or could control the furnace by adjusting a target temperature set at the thermostat. In such a situation, the thermostat may also be equipped with wireless or wired communication capabilities, e.g., Wi-Fi, Z-Wave, ZigBee, Bluetooth, HomePlug, Ethernet, USB, or other wired protocols based on the RS232, RS485, and/or RS422 standards.

In some implementations, $CO_2$ concentration data obtained from a property can be used to develop an air flow model of the property. Such an air flow model can be used to determine sources of $CO_2$ within a property, to troubleshoot a property's HVAC system, insulation, or ventilation, or to determine other activity within a property. For example, the rate of decline in $CO_2$ concentration within a property, when there is no combustion, is an indication of the air turnover within a property. Thus, a property with a tighter envelope, e.g., with less ventilation, will have a less rapid decline than a property with a draftier envelope. Additionally, information from multiple $CO_2$ sensors throughout a property can indicate directions of air flow within the property. Thus, sensors that are closer to a $CO_2$ source can indicate increased $CO_2$ concentrations before sensors further from the $CO_2$ source, thus providing insight into the cause of increases in $CO_2$ concentration. Air flow models can also be used to determine conditions or the status of a property. For example, a change in the air flow model of a property can be an indicator that a door or window has been opened at the property, that a furnace or ventilation fan has been turned on, or can indicate other conditions relating to the property. In some implementations, data obtained from $CO_2$ sensors within a property can be combined with data obtained by temperature sensors, a thermostat, or other sensors within a property to generate a more comprehensive model of a property, e.g., an entire thermodynamic model of the property.

In some implementations, information obtained by the monitoring system and analysis performed by the monitoring system, including air flow models of the property, can be used to perform troubleshooting at the property. For example, information obtained by the monitoring system can be used to determine that a natural gas range has been left on by a user of the property, can be used to identify a problem with a control mechanism of a furnace or range, can be used to determine that a pilot light is out in a furnace or range, can be used to determine areas of poor insulation in the property, to determine that a window or door is cracked or open at the property, etc.

Data obtained by $CO_2$ sensors and analysis performed by the monitoring system can be used in some implementations to determine human activity at a property. Based on the fact that humans emit $CO_2$ and that such $CO_2$ emission is dependent upon an individual's level of activity, $CO_2$ data obtained from a property can be used to determine the presence of users at a property and the level of activity of the users. For example, the monitoring system may detect a slight increase in $CO_2$ concentration within a property and determine that at least one user has entered the property. Additionally, if a $CO_2$ sensors in the user's bedroom indicates a rather large change in $CO_2$ concentration, the monitoring system may determine that a user is exercising in the bedroom, while if the $CO_2$ sensor in the user's bedroom indicates a rather small change in $CO_2$ concentration within the property, the monitoring system may determine that the user is sleeping in the bedroom. Similarly, moderate increases in $CO_2$ concentration during the middle of the night may indicate that the user is tossing and turning in bed rather than sleeping soundly. Such trends in $CO_2$ concentration may be correlated to resident activity within the property based on the understanding that humans breathe less air when they are sleeping than when they are awake. Additionally, humans tend to breathe more when they are ill than when they are healthy, allowing the monitoring system to detect potential illnesses before they progress.

Based on the monitoring system determining patterns of $CO_2$ concentration within a property that are based on user activity at the property, the monitoring system can determine patterns of activity at the property. For example, the monitoring system can determine that a user frequently returns home at 6:00 PM and begins cooking dinner by 6:30 PM, based on $CO_2$ concentrations at the property indicating a slight increase in $CO_2$ around 6:00 PM on most days and a more considerable increase in $CO_2$ concentration around 6:30 PM corresponding to a range being turned on. In some implementations, the monitoring system can perform operations based on detecting abnormalities in the $CO_2$ concentration at a property in comparison to an established pattern of $CO_2$ concentration at the property. For example, based on determining that a $CO_2$ concentration at the property has remained above a typical $CO_2$ concentration for a threshold period of time without detecting a user returning to the property, the monitoring system can determine to notify the proper authorities of a possible risk at the property. In another example, if the monitoring system determines that a user has shown above average activity for a period of multiple hours within a room of the property, the monitoring system can determine that the user may be an elderly person that has fallen in the room and can notify proper authorities based on the determination.

In some implementations, based on the monitoring system determining patterns of $CO_2$ concentration within a property that are associated with user activity, the monitoring system can determine a behavioral profile for a user of the property. For example, $CO_2$ concentration data collected from various zones of a property can indicate when a user arrives or leaves the property, is exercising at the property, cooking at the property, sleeping at the property, etc., and the monitoring system can establish a behavior profile for the user based on the received $CO_2$ concentration data. In some implementations, the behavior profile can be used to determine actions performed by the monitoring system or used to determine the control of appliances and/or HVAC system components associated with a property. For example, based on a behavior profile indicating that a user typically returns home at 6:00 PM, and based on the monitoring system determining a current time of 5:30 PM and a current $CO_2$ concentration within the property that is 500 PPM above a target $CO_2$ concentration for the property, the monitoring system can control appliances and/or HVAC system components to reduce the $CO_2$ concentration within the property. Similarly, the behavioral profile can be used to perform health monitoring if $CO_2$ levels within a property indicate that a user's behavior is abnormal, e.g., that the user is emitting above normal amounts of $CO_2$ in one room for an extended period of time indicating that they may have fallen and are struggling to stand up.

In some implementations, a behavior profile and/or $CO_2$ concentration data can be integrated with other monitoring systems used to monitor the health of users of a property. For example, the $CO_2$ concentration data can be integrated with heart rate monitor data associated with a user of the property to provide additional data regarding the user's state of health. In some instances, $CO_2$ concentration data can be integrated with other activity data, e.g., data obtained by one or more motion sensors or cameras, used to monitor the safety of the user, or can be integrated with other systems used to monitor the health of the user.

Determining activity, activity profiles, and/or user behavior profiles associated with a property can be performed based on a combination of $CO_2$ concentration data and data obtained from other sensors of a property. For example, the monitoring system can include other sensors, such as motion sensors, temperature sensors, humidity sensors, ambient light sensors, sound sensors, etc., and can use information provided by those other sensors to determine activity, activity profiles, and user behavior profiles associated with a property. As an example, motion data from a property can indicate that from the hours of 6:00 PM to 7:00 PM there is activity in the kitchen of a property and $CO_2$ concentration data can indicate that there an increase in $CO_2$ concentration within the property at the same time. Based on this data, the monitoring system can determine that the increase in $CO_2$ concentration at the property during those times is likely due to users of the property using a stove in the kitchen of the property. Similar methods can be used to develop activity profiles for a property, e.g., activity profiles indicating that users of the property are typically cooking from 6:00 PM to 7:00 PM, or to develop behavior profiles associated with one or more users of the property, e.g., motion and/or $CO_2$ concentration data that collectively indicate that the one or more user typically cook from 6:00 PM to 7:00 PM and exercise from 9:00 PM to 10:00 PM.

In some implementations, human activity information can be used by the monitoring system to control $CO_2$ concentrations within a property. For example, a target $CO_2$ concentration for a property may be 600 PPM, and various rooms of a property may have slightly varying $CO_2$ concentrations. For example, a kitchen may have a $CO_2$ concentration of 1000 PPM, a bedroom a concentration of 500 PPM, and a laundry room a concentration of 800 PPM. Based on determining that a user is in the kitchen, the monitoring system can control appliances and/or HVAC components of the property to reduce the $CO_2$ concentration at the property. If, however, the monitoring system determines that the user is located in the bedroom, the monitoring system may determine not to perform operations related to decreasing the $CO_2$ concentration within the property.

In some implementations, additional factors can influence $CO_2$ concentrations within a property, and the monitoring system can identify such factors in order to properly respond to changes in $CO_2$ concentration and/or to properly analyze $CO_2$ concentration data. For example, a pet may reside at the property in addition to one or more users of the property, and the monitoring system may perform operations to differentiate the activity of the pet from the activity of the one or more users. In some implementations, changes in $CO_2$ concentration that are detected in association with the activity of a pet can be differentiated from changes in $CO_2$ concentration that are detected in association with the activity of a user based on the changes in $CO_2$ concentration being indicative of the pet and not indicative of the user.

For instance, the monitoring system can determine a first "signature" that indicates the extent to which the activity of the pet affects $CO_2$ concentrations within the property, e.g., when the pet is active in a particular room of the property, the $CO_2$ concentration typically increases by approximately 100 PPM, and a second "signature" that indicates the extent to which activity of the user affects $CO_2$ concentrations within the property, e.g., when the user is active in the particular room of the property, the $CO_2$ concentration typically increases by approximately 200 PPM. Based on detecting an increase of 100 PPM in the particular room of the property, the monitoring system can determine that the increase in $CO_2$ concentration is likely due to the activity of the pet and not the activity of the user. Thus, the monitoring system may not include the event associated with the increase in $CO_2$ concentration in determining a behavioral profile for the user, in adjusting a target $CO_2$ concentration for the particular room, or in performing other operations typically performed in conjunction with detecting the activity of the user within the particular room, but may perform other operations in response to detecting the presence of the pet in the particular room.

In some examples, data obtained from sensors other than $CO_2$ sensors can be used to differentiate the activity of a pet from the activity of a user. For example, data obtained from motion sensors and/or video cameras at a property can be obtained and analyzed to differentiate the activity of a pet from the activity of a user. For example, image processing may be performed to determine that a shape of an object captured by a video camera is indicative of a pet and not a person, or motion sensor data can be analyzed to determine that the motion of a detected object is indicative of a pet, e.g., based on the object's rate of motion, how erratically the object moves, etc. In some implementations, a behavioral profile associated with the pet can be determined by the monitoring system, and activity detected at the property by the $CO_2$ sensors or otherwise can be compared with the pet's behavioral profile to determine whether the activity is indicative of the pet or of a user.

Other factors that influence the monitoring of $CO_2$ concentrations within a property can be addressed by the monitoring system. For example, based on $CO_2$ gas being heavier than air, $CO_2$ concentrations in low elevation areas within a property, e.g., in a basement, tend to have higher concentrations of $CO_2$ than higher elevation areas within a property, e.g., in an upstairs bedroom. The monitoring system can address this fact in analyzing $CO_2$ concentration data. For example, baseline $CO_2$ concentrations can be measured by the monitoring system to determine a typical difference in $CO_2$ concentrations between different floors of a property, and changes in CO2 concentration within the property can be analyzed in reference to the baseline CO2 concentrations. In some implementations, the monitoring system may leverage this fact to determine a possible source of CO2 at a property. For example, an increase in CO2 concentration that is only detected in a basement of a property may indicate that the increase in CO2 is associated with an event occurring in the basement, e.g., that a furnace in the basement has been turned on, while an increase in CO2 concentration that is first detected on a first floor of a property and then detected in the basement of the property may indicate that the increase in CO2 concentration is associated with an event occurring on the first floor of the property, e.g., that a stove in a first floor kitchen of the property has been turned on. In practice, the fact that CO2 is heavier than air may be considered for other purposes, e.g., when determining an air flow model for a property based on CO2 concentration data, the air flow model may compensate for the fact that air would flow differently through the property than CO2, due to CO2 being heavier than air.

CO2 concentration information obtained by a monitoring system can be monitored by a service provider associated with the monitoring system. For example, a maintenance service, elderly care service, technician, installer, or other service provider can have access to data obtained by the monitoring system and can perform actions based on the accessed data. For example, a monitoring service can monitor CO2 concentrations at a property and can notify proper authorities if an extremely elevated CO2 concentration is detected by the monitoring system. In another example, an elderly care service can attempt to contact users of a property based on a user showing increased activity in a room of the property for an extended period of time, which is indicative of a user potentially falling and not being able to help himself or herself. In still another example, a home maintenance service can access CO2 concentration data to determine possible insulation faults at the property that can be fixed by repairing the insulation, installing new windows, etc.

In some implementations, CO2 concentration data obtained by the monitoring system can be used to confirm events reported by other sensors associated with a property, both for purposes of confirming detected events and conditions, e.g., environmental conditions, at the property as well as for performing diagnostics on sensors systems associated with the property. For example, in some instances, CO2 concentration data can verify data detected by other sensors associated with a property. Motion that is detected within a property, for instance, can be confirmed as relating to users of the property being active within the property based on CO2 concentration data that indicates that users are now active at the property, e.g., based on the CO2 concentration within the property increasing by an amount that typically correlates to users being active at the property.

Similarly, CO2 concentration data can be used to determine whether other sensors, e.g., motion, temperature, humidity, or other sensors, associated with a property are operating properly. For example, motion sensor data that reports activity in a zone of the property can be compared with CO2 concentration data for the zone of the property. If the CO2 concentration data indicates that there is likely no user activity in the zone of the property, e.g., based on the CO2 concentration having not changed during the time when the motion sensor data indicates that there is user activity in the zone of the property, the monitoring system can determine that the motion sensor may be malfunctioning. Based on determining that the motion sensor may not be operating properly, the monitoring system can determine to alter the operation of the monitoring system, appliances, and/or HVAC system components associated with the property, or can determine to provide a notification to users of the property that the motion sensor may not be operating properly. In practice, other actions can be performed by the monitoring system based on determining that one or more sensors associated with the property may be malfunctioning, e.g., the monitoring system may contact a service provider associated with the property to report the potentially damaged sensors.

As the monitoring system features a number of sensors, including CO2 sensors and other sensors, e.g., motion sensors, temperature sensors, humidity sensors, etc., the limitations of these sensing mechanisms may be compensated for by the monitoring system. Specifically, with respect to CO2 sensors, the settling time of the sensors, e.g., the latency of the CO2 sensors in responding to changes in CO2 concentration, and the presence of noise in the sensor output may be considered. For example, in some instances, to adjust for the latency of CO2 sensors in responding to changes in CO2 concentration, a characterization of the CO2 sensors may be performed or information characterizing the operation of the CO2 sensors may be available to the monitoring system. In analyzing CO2 concentration data obtained by the sensors, the characteristics of the sensors can be used to normalize, filter, or otherwise manipulate the CO2 concentration data to ensure that the monitoring system properly addresses changes in CO2 concentration.

For instance, characteristics of a CO2 sensor may indicate that the CO2 sensor can detect changes in CO2 concentration up to a maximum rate of change or a maximum concentration, e.g., the fastest change in CO2 concentration that the CO2 sensor may be able to accurately report is a rate of change of 100 PPM per minute, and a maximum concentration that the CO2 sensor may be able to accurately report is a CO2 concentration of 5000 PPM. Based on these characteristics, the monitoring system may interpret rates of change in CO2 concentration that are equal to 100 PPM per minute as being likely greater than the reported rate of change in CO2 concentration, e.g., if the CO2 sensor reports a rate of change of CO2 concentration of 100 PPM per minute, the monitoring system may determine that the actual rate of change is above 100 PPM per minute. Similarly, the monitoring system may interpret reported CO2 concentration of 5000 PPM as likely being above that concentration. In addition, such characteristics may be used to perform signal processing on CO2 concentration data. For example, noise in the CO2 sensor output may be random noise that has a high frequency or results in changes in CO2 concentration that are near or at 100 PPM per minute for very short periods of time, e.g., from one sample to the next. The monitoring system may be able to process the CO2 sensor output such that the perceived changes in CO2 concentration at the property due to noise does not interfere with the monitoring system's ability to properly react to changes in CO2 concentration at the property, or rates of change in CO2 concentration at the property. For example, the monitoring system may perform a running average on CO2 concentration data, may perform filtering on the CO2 concentration data, or may perform other operations to remove signal noise from the CO2 concentration data to enable the monitoring system to properly respond to changes in CO2 concentration.

While described in this document with respect to CO2 concentrations, the methods and systems described can also be used to monitor the presence of other gases or chemicals at a property. For example, a similar system can monitor oxygen levels at a property for air quality control, can monitor carbon monoxide levels at a property for safety concerns, can monitor the presence of harmful gases, e.g., chlorine gas, or can be used to monitor and perform actions based on the presence of other chemicals at a property.

The described systems, methods, and techniques may be implemented in digital electronic circuitry, computer hardware, firmware, software, or in combinations of these elements. Apparatus implementing these techniques can include appropriate input and output devices, a computer processor, and a computer program product tangibly embodied in a machine-readable storage device for execution by a programmable processor. A process implementing these techniques can be performed by a programmable processor executing a program of instructions to perform desired functions by operating on input data and generating appropriate output. The techniques can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing can be supplemented by, or incorporated in, specially designed application-specific integrated circuits (ASICs).

It will be understood that various modifications can be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A system for processing carbon dioxide sensor data in combination with additional sensor and automation control data, the system comprising:
a monitoring system that is configured to monitor a fixed property, that includes a carbon dioxide sensor associated with the monitoring system, that includes one or more additional sensors that are installed at the fixed property and that are configured to sense attributes of the fixed property, and that includes one or more automation control components configured to control one or more appliances located at the fixed property; and
a monitoring application server that is configured to electronically receive, either directly or via a network communications module, data communications based on carbon dioxide sensor data captured by the carbon dioxide sensor, additional sensor data captured by the one or more additional sensors installed at the fixed property, and automation control data related to the one or more automation control components, the monitoring application server being configured to perform operations comprising:
integrating the carbon dioxide sensor data with the additional sensor data and the automation control data;
analyzing the integrated carbon dioxide sensor data, additional sensor data, and automation control data; and
performing an operation related to the fixed property based on the analysis of the integrated carbon dioxide sensor data, additional sensor data, and automation control data.

2. The system of claim 1, wherein performing the operation related to the fixed property based on the analysis of the integrated carbon dioxide sensor data, additional sensor data, and automation control data comprises automatically, without human intervention, controlling at least one of the one or more automation control components to control an appliance located at the fixed property based on the analysis of the integrated carbon dioxide sensor data, additional sensor data, and automation control data.

3. The system of claim 1, wherein performing the operation related to the fixed property based on the analysis of the integrated carbon dioxide sensor data, additional sensor data, and automation control data comprises sending, to a mobile device of at least one user of the fixed property, a notification based on the analysis of the integrated carbon dioxide sensor data, additional sensor data, and automation control data.

4. The system of claim 1, wherein performing the operation related to the fixed property based on the analysis of the integrated carbon dioxide sensor data, additional sensor data, and automation control data comprises plotting, on a graph, a representation of the carbon dioxide sensor data over time in combination with corresponding sensor and automation control events reflected in the additional sensor data and the automation control data.

5. The system of claim 1, wherein performing the operation related to the fixed property based on the analysis of the integrated carbon dioxide sensor data, additional sensor data, and automation control data comprises determining an air flow model for the fixed property based on the analysis of the integrated carbon dioxide sensor data, additional sensor data, and automation control data.

6. The system of claim 1:
wherein analyzing the integrated carbon dioxide sensor data, additional sensor data, and automation control data comprises:
accessing, from electronic storage, a target carbon dioxide concentration level for the fixed property;
accessing, from electronic storage, a schedule of expected usage of the fixed property that includes expected appliance usage and expected occupancy of the fixed property; and
analyzing the integrated carbon dioxide sensor data, additional sensor data, and automation control data with respect to the target carbon dioxide concentration level and the schedule of expected usage of the fixed property;
wherein performing the operation related to the fixed property based on the analysis of the integrated carbon dioxide sensor data, additional sensor data, and automation control data comprises automatically, without human intervention, controlling at least one of the one or more automation control components to control an appliance located at the fixed property in a manner directed to reducing carbon dioxide concentration in the fixed property based on the analysis of the integrated carbon dioxide sensor data, additional sensor data, and automation control data with respect to the target carbon dioxide concentration level and the schedule of expected usage of the fixed property revealing that the target carbon dioxide concentration level is likely to be exceeded in view of the schedule of expected usage of the fixed property.

7. The system of claim 1, wherein performing the operation related to the fixed property based on the analysis of the integrated carbon dioxide sensor data, additional sensor data, and automation control data comprises detecting human activity within the fixed property based on a combination of the carbon dioxide sensor data and the additional sensor data suggesting human activity within the fixed property.

8. The system of claim 7, wherein detecting human activity within the fixed property based on a combination of the carbon dioxide sensor data and the additional sensor data suggesting human activity within the fixed property comprises determining a behavioral profile for one or more humans associated with the fixed property based on the detected human activity, the behavioral profile indicating sleep activity, eating activity, and exercising activity of the one or more humans inferred through a combination of the carbon dioxide sensor data, additional sensor data, and automation control data.

9. The system of claim 1:
wherein analyzing the integrated carbon dioxide sensor data, additional sensor data, and automation control data comprises detecting an abnormality in the carbon dioxide sensor data; and
wherein performing the operation related to the fixed property based on the analysis of the integrated carbon dioxide sensor data, additional sensor data, and automation control data comprises performing an operation related to the fixed property based on the detection of the abnormality in the carbon dioxide sensor data.

10. The system of claim 1:
wherein analyzing the integrated carbon dioxide sensor data, additional sensor data, and automation control data comprises:
detecting an event based on the additional sensor data, and
confirming the detected event by determining that the carbon dioxide sensor data is consistent with the detected event; and
wherein performing the operation related to the fixed property based on the analysis of the integrated carbon dioxide sensor data, additional sensor data, and automation control data comprises performing an operation related to the fixed property based on the confirmation of the detected event.

11. The system of claim 1:
wherein analyzing the integrated carbon dioxide sensor data, additional sensor data, and automation control data comprises assessing whether the carbon dioxide sensor data aligns with what would have been expected given usage of the one or more appliances indicated by the automation control data; and
wherein performing the operation related to the fixed property based on the analysis of the integrated carbon dioxide sensor data, additional sensor data, and automation control data comprises performing an operation related to the fixed property based on the assessment of whether the carbon dioxide sensor data aligns with what would have been expected given usage of the one or more appliances indicated by the automation control data.

12. The system of claim 11:
wherein assessing whether the carbon dioxide sensor data aligns with what would have been expected given usage of the one or more appliances indicated by the automation control data comprises determining that the carbon dioxide sensor data does not align with what would have been expected given usage of the one or more appliances indicated by the automation control data; and
wherein performing the operation related to the fixed property based on the assessment of whether the carbon dioxide sensor data aligns with what would have been expected given usage of the one or more appliances indicated by the automation control data comprises providing a notification that at least one of the one or more appliances is malfunctioning based on the determination that the carbon dioxide sensor data does not align with what would have been expected given usage of the one or more appliances indicated by the automation control data.

13. The system of claim 1, wherein the one or more automation control components are configured to control one or more of a range, an oven, and a heating, ventilation, and air conditioning system located at the fixed property.

14. The system of claim 1, wherein the monitoring system is a security system installed in a building, the security system being configured to detect an alarm event based on the additional sensor data.

15. The system of claim 1, wherein the one or more additional sensors include at least one of a contact sensor, a motion sensor, a glass breaker sensor, a temperature sensor, a smoke sensor, or a panic button sensor.

16. A method comprising
accessing, by at least one processor, a carbon dioxide sample measured by a carbon dioxide sensor located in a fixed property;
comparing, by the at least one processor, the carbon dioxide sample to one or more prior samples measured by the carbon dioxide sensor located in the fixed property;
determining, by the at least one processor, that carbon dioxide concentration in the fixed property has increased by at least a first threshold amount;
based on the determination that the carbon dioxide concentration in the fixed property has increased by at least the first threshold amount, starting a timer;
determining that the timer has reached a first threshold period of time without detection of a decrease in the carbon dioxide concentration in the fixed property; and
based on the determination that the timer has reached the first threshold period of time without detection of a decrease in the carbon dioxide concentration in the fixed property, presenting an alarm using an output device located in the fixed property and logging, in electronic storage, an increased carbon dioxide event in a history of carbon dioxide events.

17. The method of claim 16, further comprising:
determining that the timer has reached a second threshold period of time without detection of a decrease in the carbon dioxide concentration in the fixed property, the second threshold period of time being greater than the first threshold period of time; and
based on the determination that the timer has reached the second threshold period of time without detection of a decrease in the carbon dioxide concentration in the fixed property, sending, to a mobile device of at least one user of the fixed property, a notification indicating increased carbon dioxide concentration in the fixed property.

18. The method of claim 17, further comprising:
determining that the timer has reached a third threshold period of time without detection of a decrease in the carbon dioxide concentration in the fixed property, the third threshold period of time being greater than the second threshold period of time; and
based on the determination that the timer has reached the third threshold period of time without detection of a decrease in the carbon dioxide concentration in the fixed property, alerting an appropriate emergency services authority to the increased carbon dioxide concentration in the fixed property.

19. The method of claim 16, further comprising:
determining, by the at least one processor, that carbon dioxide concentration in the fixed property has decreased by at least a second threshold amount; and
based on the determination that the carbon dioxide concentration in the fixed property has decreased by at least the second threshold amount, stopping the timer and logging, in electronic storage, a decreased carbon dioxide event in the history of carbon dioxide events.

20. The method of claim 19:
wherein logging the increased carbon dioxide event in the history of carbon dioxide events comprises logging first data that indicates a first carbon dioxide level associated with the increased carbon dioxide event and a first time of the increased carbon dioxide event; and
wherein logging the decreased carbon dioxide event in the history of carbon dioxide events comprises logging second data that indicates a second carbon dioxide level associated with the decreased carbon dioxide event and a second time of the decreased carbon dioxide event.

\* \* \* \* \*